Dec. 25, 1945. F. H. HOWARD Plant Pat. 665
ROSE PLANT
Filed Dec. 16, 1944
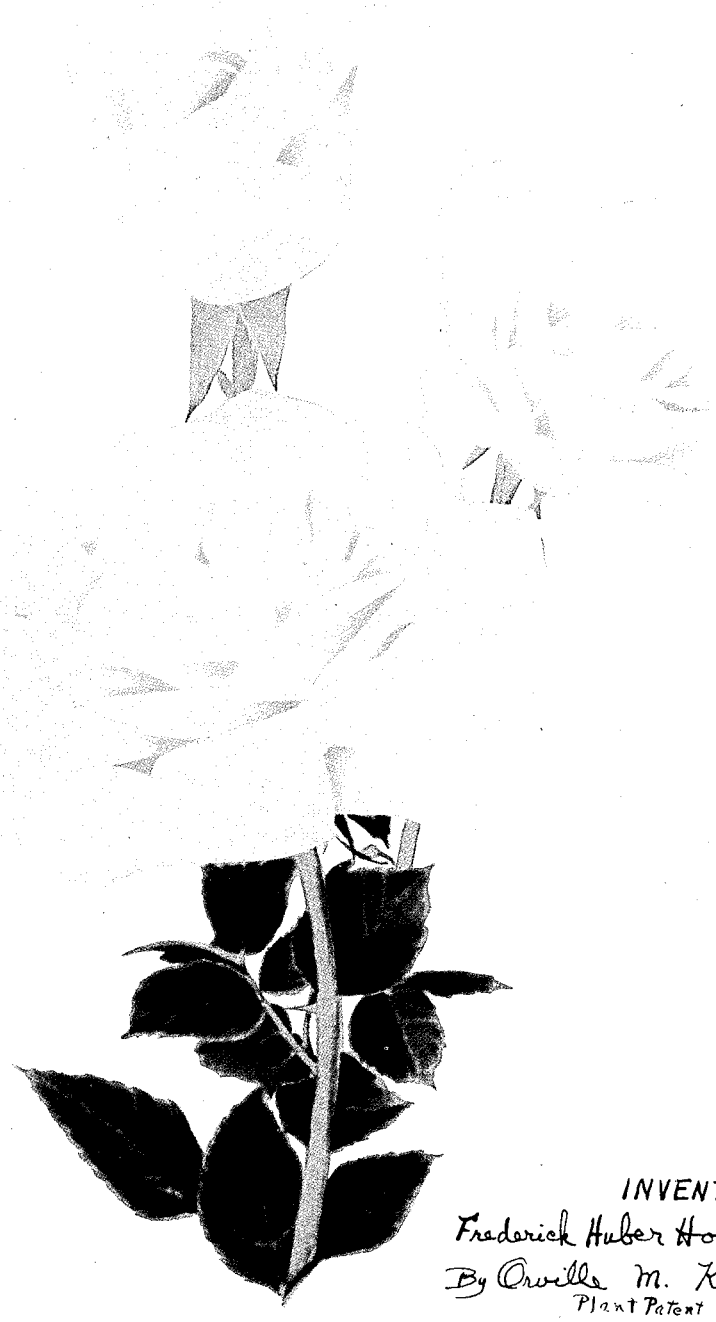
INVENTOR
Frederick Huber Howard
By Orville M. Kile
Plant Patent Agt.

Patented Dec. 25, 1945

Plant Pat. 665

UNITED STATES PATENT OFFICE

665

ROSE PLANT

Frederick Huber Howard, Montebello, Calif., assignor to Howard & Smith, Montebello, Calif.

Application December 16, 1944, Serial No. 568,485

1 Claim. (Cl. 47—61)

My present invention relates to a new and distinct variety of hybrid tea rose plant possessing a novel combination of desirable characteristics. It is a line bred hybrid resulting from a cross between Mrs. J. D. Eisle as the seed parent and President Hoover as the pollen parent, the cross having been made by me at the green houses of Howard & Smith in Montebello.

Among its most outstanding characteristics are its distinct color and intense fragrance of flower, its very free blooming habit, and its resistance to disease.

The accompanying illustrations show three specimens in various stages of opening and in as nearly the true colors as the artist was able to portray them. The color of the rose varies slightly at different seasons of the year, these specimens having been painted in the early fall from field-grown roses.

Following is a detailed description of this new variety of rose plant.

*The plant*

Growth habits: Exceedingly vigorous grower, sending out numbers of small basal canes which in a single season attain an average height of 3½ to 4 feet. Growth is compact, the plant being somewhat columnar in contour. Lateral shoots are freely produced on the upper portion of the plant after the terminal crop of bloom has passed. Lateral shoots attain a good length—10 to 12 inches—under normal conditions of outdoor culture.

Blooming habits: Continuous and free bloomer.

Foliage: Normal quantity. Leaves have 3 to 7 leaflets.

*Texture.*—Leathery.

*Size.*—Very small, terminal leaflet of top cluster, 1 to 1¼ inches long.

*Color.*—Approximately Elm Green (Plate XVII, Ridgway's Color Standards).

*Shape.*—Almost round, with finely serrated edge.

*Rachis.*—Slender; grooved above; sharp spines below.

*Stipules.*—Long; clinging; narrow.

Stems: Stiff; upright; long.

*Color.*—Approximately Calla Green (Plate V, Ridgway's Color Standards).

*Thorns.*—Many; stiff; sharp; brownish; pointing almost straight outward.

*The bloom*

Bud:

*Size.*—Just as calyx breaks it is slightly less than an inch in length. Just before unfurling it is from 1½ to 1¾ inches long.

*Shape.*—Conical with broad base and pointed tip; perfect in form.

*Opening.*—Opens slowly and evenly.

*Peduncle.*—Straight; heavy; short, bringing foliage close to flower; covered with thorns and spines; bronzed.

*Sepals.*—Broad; points extend beyond breaking bud; sometimes foliaceous; reflex early.

*Color.*—Crimson (22) at base, ranging to (22/2) at edges of petals. (Horticultural Colour Chart.)

Flower:

*Borne.*—Singly or in small groups.

*Size.*—Medium. Grown in the open field in my nurseries, the diameter is usually from 3½ to 4½ inches.

*Form.*—Half-open rose is full and deep, usually with the center still pointed. Later it opens showing an informal, irregular arrangement of slightly undulant, evenly disposed petals which open flat and finish flat without curling.

*Petalage.*—Petalage varies considerably in different specimens. The average is about 30 petals.

*Color.*—Varies somewhat at different times of the year. The most prevalent color is that of the specimens shown and is approximately an over-all tint which lies between Crimson (22/1) and (22/2) of Horticultural Colour Chart, with a vivid yellow aiglet which suffuses into the Crimson to produce a coppery shade approximately Tangerine Orange.

Petals:

*Size.*—Outer petals approximately 1¾ inches by 1¾ inches.

*Shape.*—The outer petals are almost round and are deeply cupped. Inner petals are narrower, smaller and not so deeply cupped.

*Arrangement.*—Imbricated and informal in center.

*Behavior.*—Cling tenaciously without curling.

Fragrance: Intense but not overpowering.

Longevity: Excellent.

Reproductive organs:

*Pistils.*—Many; tightly bunched. *Styles*—short and greenish white. *Stigmas*—red with small yellow tip.

*Stamens.*—Irregularly bunched about the pistils. *Filaments*—uneven in length; color dark orange at base ranging to yellow at top. *Anthers*—large and deep yellow.

Having thus disclosed my invention, I claim:

The new and distinct variety of hybrid tea rose plant herein shown and described, characterized particularly by its intensely healthy and vigorous growth, its free blooming habit; its perfectly formed bud; and its flowers having intense fragrance, distinctive bright pink color and open form.

FREDERICK HUBER HOWARD.